United States Patent
Hockings

(10) Patent No.: US 10,765,318 B2
(45) Date of Patent: Sep. 8, 2020

(54) METHOD FOR TREATING AND REVERSING TYPE 2 DIABETES

(71) Applicant: J. Murray Hockings, Colleyville, TX (US)

(72) Inventor: J. Murray Hockings, Colleyville, TX (US)

(*) Notice: Subject to any disclaimer, the term of this patent is extended or adjusted under 35 U.S.C. 154(b) by 229 days.

(21) Appl. No.: 15/590,809

(22) Filed: May 9, 2017

(65) Prior Publication Data
US 2018/0325374 A1 Nov. 15, 2018

(51) Int. Cl.
*A61B 5/00* (2006.01)
*A23L 33/00* (2016.01)
*G09B 29/00* (2006.01)

(52) U.S. Cl.
CPC ............... *A61B 5/00* (2013.01); *A23L 33/30* (2016.08); *A23L 33/40* (2016.08); *G09B 29/00* (2013.01)

(58) Field of Classification Search
None
See application file for complete search history.

(56) References Cited

PUBLICATIONS https://web.archive.org/web/20160405063146/http://helpyourdiabetes.com/, [Apr. 5, 2016], retrieved using Waybackmachine Internet Archive.

*Primary Examiner* — Sergio Coffa
(74) *Attorney, Agent, or Firm* — Carter Ledyard & Milburn, LLP

(57) ABSTRACT

Contrary to popular belief, diabetes can be reversed through diet and lifestyle changes. The purpose of the present invention is to provide a method to reduce or eliminate the medication intake of a patient with Type 2 Diabetes. This can also lead to the loss of weight and regaining energy levels. The present invention provides a novel and very effective regimen for treatment of Type 2 diabetes not previously available. It is a further object of the present invention to treat Type 2 diabetes with the combination of a specific meal plan, an exercise regimen and specific supplements for cleansing and overcoming bodily deficiencies.

7 Claims, No Drawings

METHOD FOR TREATING AND REVERSING TYPE 2 DIABETES

The present invention relates to a method of treating Type II diabetes, more specifically a regimen to be followed consisting of exercise, a specific meal plan and supplements.

BACKGROUND

More than 29 million Americans are currently living with diabetes and 25% of them are unaware they even have it. About 86 million Americans are living with pre-diabetes which is a serious health condition that increases one's risk of Type 2 diabetes and other chronic illnesses. The CDC is working to reverse the US diabetes epidemic by tracking disease trends, focusing on prevention, identifying effective treatments and improving medical care.

There are two types of diabetes, Type 1 and Type 2. A patient with Type 1 diabetes does not produce sufficient amounts of insulin. Patients with Type 2 diabetes are unable to properly use insulin. Type 2 diabetes develops when the body becomes resistant to insulin or when the pancreas stops producing enough insulin. Insulin is a hormone produced in the pancreas that regulates the amount of glucose in the blood. Insulin circulates into the bloodstream and allows the glucose to enter the cells where it can be used for energy. When the body lacks sufficient insulin or is unable to effectively use the insulin, glucose builds up in the bloodstream producing high glucose levels.

More than 20% of health care spending is for people diagnosed with diabetes. Type 2 diabetes accounts for 90-95% of the diagnosed diabetes cases. The life expectancy of people with diabetes in 2004 was lower than that for the general population by about 15 years. Over time, if not properly watched and attended to, Type 2 diabetes can lead to serious problems with blood pressure, heart, nerves, eyes and kidneys.

Insulin is the primary therapy to treat Type 1 diabetes. Dietary changes, regular insulin, and medications, can be used to control blood glucose levels for patients with Type 2 diabetes.

Some people with Type 2 diabetes can achieve their target glucose levels with diet and exercise alone, but many also need diabetes medications or insulin therapy.

SUMMARY OF THE INVENTION

Contrary to popular belief, diabetes can be reversed through diet and lifestyle changes.

The purpose of the present invention is to provide a method to reduce or eliminate the medication intake of a patient with Type 2 Diabetes. This can also lead to the loss of weight and regaining energy levels.

The present invention provides a novel and very effective regimen for treatment of Type 2 diabetes not previously available.

It is a further object of the present invention to treat Type 2 diabetes with the combination of a specific meal plan, an exercise regimen and specific supplements for cleansing and overcoming bodily deficiencies.

DETAILED DESCRIPTION

Reversal of Type 2 diabetes can be achieved following the method of the present invention. The present invention is a nutritional wellness program that assists in normalizing metabolism and stabilizes blood sugar levels by a combination of a meal plan, a cleanse, exercise, a personalized report based on individual lab results, natural supplement support customized for diabetics for bodily deficiencies, and unlimited phone support and coaching with a doctor. The scale of improvements are determined by the patient's ability to reduce or eliminate diabetic medications, blood pressure medications, and to lose weight. The method of the present invention helps patients with Type 2 diabetes get off their medications which damage their bodies the longer they are on them.

The meal plan of the present invention is designed to assist in the reversal of diabetes. The specific meal plan provided should be followed by the patient for life. The meal plan consists of eating specific foods and avoiding specific foods. Foods that can be enjoyed on the meal plan include: cream of buckwheat; vegetables (no potatoes except for sweet potatoes and yams); beans and legumes (except for soybeans); meats with no additives (limit pork intake); eggs; nuts and seeds (including nut butters); *Quinoa*; Amaranth; sweeteners such as raw honey (limited), molasses, *stevia* (with no additives); herbal and caffeine free teas; unsweetened almond milk; unsweetened coconut milk; lemon juice; lime juice; purified water and fresh or frozen fruit (no sugars or sweeteners added, limit pineapple, watermelon, and bananas. Fruits must be eaten with a protein or fat and prior to 3 pm).

The foods to be avoided on the meal plan in the present invention include: all dairy (including milk, cheese, butter, sour cream yogurt, ice cream, cottage cheese, etc.); all wheat/rye/oat/barley (such as pasta, bread, rice, buns, rolls, cereal, bagel, crackers, oatmeal etc.); all soy products (including tofu, soymilk, soybeans, edamame, and soy nuts); all corn (fresh, frozen, popcorn etc.); all red and white potatoes; all alcohol; all juices (except for lemon juice and lime juice); all caffeine (including coffee, green and black tea, soda, red bull, etc., no de-caffeinated or caffeinated variations.); all carbonated beverages and sodas (including sparkling water and club soda); all sugar and artificial sweeteners (including dextrose, fructose, white sugar, brown sugar, any type of corn syrup, acesulfame potassium (acesulfame K), Splenda (sucralose), Sweet'N Low (saccharin), Nutrasweet (aspartame), and Equal (aspartame)).

The cleanse of the present invention consists of taking the natural supplements HYD PRO-Cleanse and HYD PRO-Gluco for the first 30 days of the program. HYD PRO-Cleanse is a therapeutic nutritional formula for bowel detoxification and digestive lining support. This supplement safely removes toxins from the body without the side effects associated with cleansing. Most products today use a fiber base supplement to push toxins and metals out of the system. However, there is a risk of the toxins re-depositing in the tissue before it is eliminated from the body. HYD PRO-Cleanse overcomes this difficulty by combining two kinds of fibers with chelating ingredients. HYD PRO-Cleanse combines non-digestive and functional fibers to surround toxins. Enzymes are used to partially digest these fibers to form a gelatinous/fiber matrix which enshrouds the toxins and escorts them out of the body. Ensuring proper elimination means the toxins don't recirculate in the body causing more unwanted reactions. Each serving, 1 capsule, of HYD PRO-Cleanse is a unique combination of 10 mcg of Zinc (as zinc amino acid chelate), 25 mcg of Copper (as copper amino acid chelate), 10 mcg of Manganese (as manganese amino acid chelate), 695 mg of an Optimal Cleanse Blend consisting of Licorice root, *Psyllium*, Oat Bran, Celery, Sweet Potato, Apple Pectin, Grapefruit Pectin and Chlorella, 10 mg of Stabilized Glutamine (magnesium glycyl glutamine) and 10 mg of Opti-Blend Delivery System. Two key binding ingredients to safely remove the toxins are the chlorella and magnesium glycl glutamine.

HYD PRO-Gluco is a therapeutic nutrition formula aiding in fat digestion and sugar balancing. It digests and metabolizes dietary and body fats as well as balance sugars and relieve cravings. Each serving, 3 capsules, of HYD PRO-Gluco contains 30 mcg of Zinc (as zinc amino acid chelate), 45 mcg of Selenium (as selenium amino acid chelate), 75 mcg of Copper (as copper amino acid chelate), 30 mcg of Manganese (as manganese amino acid chelate), 100 mcg of Chromium (as chromium amino acid chelate) 525 LU Lipase, 150 mg of Garlic (odorless bulb), 60 mg Tumeric root, 76 mg of a Proprietary Blend of Garcinia, Cambogia, Cinnamon Verum, Raspberry Ketones, *Rhodiola Crenulata* and Glucomannanase, and 30 mg of Opti-Blend Delivery System. The Lipase is necessary to break down fat and make it usable as energy in the body. The chromium and cinnamon help balance blood sugar as well as the proprietary blend to curb appetite.

In addition to the meal plan, exercise plays an important role in the present invention and also should be followed for the lifetime of the patient. The patient must exercise 30 minutes a day for at least five days a week. Such exercise can consist of walking, using the stationary bike, the treadmill or the elliptical machine. If patients are unable to walk or perform such exercises mentioned above they can also exercise by alternative means such as water assisted walking, seated aerobics, or 30 minutes of lifting soup cans over their heads for bicep curls, for example.

Diabetes depletes nutritional stores dramatically and can be referred to as a wasting disease because of the nutrient demands placed on the body. Elevated blood glucose levels cause a nutritional diuretic in vitamins and minerals that needs to be overcome. Nutritional supplementation is important in addressing diabetes issues because the body's ability to use insulin is improved with adequate amounts of nutrients in the system. The present invention uses an assortment of supplements in a precise fashion. Prior art fails to address the lost nutrient factors which can devastatingly impact the long term health of the individual fighting blood glucose issues. Since the amount of vitamins and minerals depleted are high, one would need to take multiple bottles of varying vitamins to balance the deficiencies created. The nutritional supplements of the present invention are 100% natural and are used to cleanse the body and treat such deficiencies. The supplements are HYD PRO-Cleanse, HYD PRO-Liver Kidney, HYD PRO-Gluco and HYD PRO-Health pak and are novel to the present invention.

In the present invention the patient takes natural supplements that have been customized for use by diabetics to support bodily deficiencies caused by the disease. The recommended supplements are provided to the patient in recommended dosages based on the severity of the disease amongst other factors. All patients take the supplements HYD PRO-Gluco and HYD PRO-Cleanse for the first 30 days of the program to cleanse. After following the disclosed meal plan, exercising and taking the above referenced supplements for the first 30 days, the patients then take the HYD PRO-Health Pak and the HYD PRO-Liver/Kidney supplements for between two to six months while continuing the meal and exercise plan. The amount of time the patient takes the HYD PRO-Health Pak and the HYD PRO-Liver/Kidney supplements is based on the severity of the disease. Mild cases of Type 2 Diabetes will take the HYD PRO-Health Pak and the HYD PRO-Liver/Kidney supplements for two months. Patients with a moderate case of Type 2 Diabetes will take HYD PRO-Health Pak and the HYD PRO-Liver/Kidney supplements for four months, and patients with a severe case of Type 2 Diabetes will take HYD PRO-Health Pak and the HYD PRO-Liver/Kidney supplements for six months.

HYD PRO-Liver/Kidney is a therapeutic nutritional formula for nutrient support for organ detoxification. The liver and kidneys act as the body's filtration system by helping rid the body of toxins as well as performing other necessary functions. These organs can only function properly if they are kept clean and provided with the proper nutrients. When the liver and kidneys are not nutritionally supported or adequately cleansed, the body begins to store toxins in the tissues. These toxins can cause symptoms and over time lead to chronic illnesses. HYD PRO-Liver Kidney cleanses and fortifies these organs simultaneously without any side effects typically associated with an organ cleanse. Each serving, 2 capsules, of HYD PRO-Liver/Kidney contains 40 mg of Zinc (as zinc amino acid chelate), 50 mcg of Copper (as copper amino acid chelate), 20 mcg of Manganese (as manganese amino acid chelate), 150 mg Milk Thistle Extract (80%) (seed), 200 mg Barberry root, 200 mg Dandelion root, 400 LU Lipase and 20 mg of Opti-Blend Delivery System (Amylase, Protease I, Protease II, Peptizyme SP, Lipase, Invertase, Cellulase, Lactase, Maltase, Hemiseb, Zinc AAC, Copper AAC, Manganese AAC and Molasses).

HYD PRO-Health Pak is a supplement that provides essential daily nutrients in convenient dally paks that support healthy blood sugar. Each serving of the HYD PRO-Health Paks contains 1250 IU of Vitamin A (whole food cultured), 15 mg of Vitamin C (whole food cultured), 4100 IU of Vitamin D (whole food cultured), 9.75 IU of Vitamin E (whole food cultured), 20 mcg of Vitamin K (whole food cultured), 120 mcg of Vitamin K2 (menaquinone-7), 380 mcg of Vitamin B1—Thiamine (whole food cultured), 500 mcg of Vitamin B2—Riboflavin (whole food cultured), 5 mg of Vitamin B3—Niacin (whole food cultured), 500 mcg of Vitamin B6—Pyridoxine (whole food cultured), 100 mcg of Vitamin B9—Folic Acid as Folate (whole food cultured), <10 mcg of Vitamin B12—Methylcobalamin (whole food cultured), 10 mcg of Vitamin B7—Biotin (whole food cultured), 2.5 mg of Vitamin B5—Pantothenic Acid (whole food cultured), 125 mg of Calcium (Bisglycinate Chelate), 4.5 mg of Iron—Ferrochel (Ferrous Bisglycinate Chelate), 50 mg of Magnesium (Bisglycinate Chelate), 4.04 mg of Zinc (Bisglycinate Chelate), 50 mcg of Selenium (Glycinate Complex), 650 mcg of Copper (Bisglycinate Chelate), 560 mcg Manganese (Bisglycinate Chelate), 100 mcg of Chromium (Nicotinate Glycinate Chelate), 20 mcg of Molybdenum (Glycinate Chelate), 9 mg of Potassium (Glycinate Complex), 500 mg of Stabilized Fatty Acid Blend (Borage Oil, Flaxseed Oil and Algae Oil), 415 mg of Proprietary Whole Food Cultured Media Blend including an organic vegetable blend, an organic fruit blend, vitamins and probiotics, 100 mg of garlic, 100 mg of Jerusalem Artichoke, 55 mg of Opti Blend Delivery System (Amylase, Protease I and II, Lipase, Invertase, Maltase, Cellulase, Lactase, HemiSEB, Zinc, Copper, Manganese and Molasses), 50.6 mg of Proprietary Blend (Cinnamon Verum, Raspberry Ketones, *Rhodiola Crenulata* and Glucomannanase), 40 mg of Tumeric, 30 mg of CoQ10 Ubiquinol, 5 mg of Black Strap Molasses, 40 mcg Kelp (Iodine), 175 LU of Lipase and 1.25 Billion CFU of Patented Stabilized Heat Resistant Probiotics (DDS-1, *Lactobacillus Acidophilus*, L-Plantarum, *Lactobacillus, Bulgaricus, Streptococcus Thermophilus* and *Enterococcus Faecium*).

Upon starting the program, the patient contacts the doctor at a minimum of once a week and provides their blood glucose numbers so their progress can be tracked. As the blood glucose numbers begin to drop the patient contacts their primary doctor so the formal diabetes medication dosages can be lowered. Patients also receive a weekly meal plan with recipes and a weekly training video, as well as a monthly newsletter. Three days a week the patient partakes in group support calls and has unlimited support access with the doctor by phone or email 7 days week to address any questions or concerns they may have.

The weekly meal plan provides recipes in a 4"×6" format so favorites can be cut out and pasted onto a recipe card and easily stored in a recipe box for quick and easy reference in the future. If a meal that is provided in the weekly meal plan is not liked, another recipe previously provided can be substituted in its place. Snack items may also be substituted. Any substitutions can be made as long as the meals and recipes are modified in accordance with the foods to enjoy and the food to avoid lists. If the patient continues to be hungry after eating a meal, more vegetables can be eaten until satisfied. Also, while eating, no drinking other than a few swallows of slightly cool or room temperature water should be taken with the meals, as it will impede digestion.

A shopping list is provided for easy list making where items needed can be circled or written in on one of the blank lines. Servings sizes are important and should be noted when making a recipe for the ingredients amount as well as the amount eaten.

Case Study

A case study was conducted on 20 patients following the method of the present invention. In order to participate in the study the patients had to be a diagnosed Type 2 Diabetic and currently taking diabetic medication. All of the patients of the study have A1c's ranging from 6.0 to 12.5. The average diabetic takes 6-8 medications, sometimes more depending on the individuals health situation. These medications include those for diabetes, high blood pressure, other heart issues and high cholesterol.

All people who followed the present invention reduced or eliminated their diabetic medications, lost weight, or had personally expressed having more energy. Results are based off of the diligence and compliance of each patient. If the patient was not strict, they did not see the same results of those who were. The average weight loss for the 20 patients researched was 20 pounds. Most people were able to reduce or eliminate their blood pressure medication as well. This case study also found that many people eliminated their cholesterol medication, as it was no longer necessary. Table 1, provided below, shows the individual results of the 20 patients studied including the reduction and/or elimination of medications after following the method of the present invention.

TABLE 1

| Patient | A1C Pre | A1C Post | Weight Pre | Weight Post | a1 Cholesterol Pre | a1 Cholesterol Post | Blood Pressure Pre | Blood Pressure Post | Meds/Dosage Pre | Meds/Dosage Post |
|---|---|---|---|---|---|---|---|---|---|---|
| #1 | 7 | 5.9 | 272 | 207 | 103 | 105 | NA | NA | 30 Units Lantus<br>Januvia 1/day<br>500 mg Metformin 2x/day | Off Lantus<br>Off Januvia<br>Off Metformin |
| #2 | 7.3 | 5.9 | 238 | 228 | NA | NA | 141/73 | 120/65 | Victoza 1.8<br>Metoprolol 1/day | Off Victoza<br>Off Metoprolol |
| #3 | 7 | 5.5 | 170 | 148 | 185 | 121 | 110/70 | 122/56 | 500 mg Metformin 3x/day<br>Omeprozole 20 mg/day<br>Enalapril 10 mg/day<br>Glyburide 2.5 mg/day<br>Simvastatin 80 mg | 500 mg Metformin 1x/day<br>Off Omeprozole<br>Off Enalapril<br>Off Glyburide<br>Off Simvastatin |
| #4 | 10 | 5.9 | 285.4 | 251.6 | 151 | 157 | 122/73 | 116/79 | Losartan 100 mg/day<br>Amlodipine 5 mg/day<br>Metformin 500 mg<br>L-Thyroxine 75 mcg | Off Losartan<br>Off Amlodipine<br>Off Metformin<br>Off L-Thyroxine |
| #5 | 6.8 | 4.8 | 320 | 273 | 143 | 129 | 140/62 | 110/53 | Lantus 160 units/day<br>Lisinopril 10 mg/day<br>Metoprolol 25 mg 2x/day<br>glimepiride 2 mg/day | Off Lantus<br>Lisinopril 5 mg/day<br>Off Metoprolol<br>glimepiride 1 mg/day |
| #6 | 11 | 5.3 | 197 | 147 | 208 | 152 | 114/72 | 118/70 | Januvia 100 mg 2/day<br>Lisinopril 40 mg/day<br>Bisoprolol 5-6.25/day | Off Januvia<br>Off Lisinopril<br>Off Bisoprolol |
| #7 | 8 | 5.3 | 307 | 277 | 181 | 131 | 124/84 | 126/79 | Metoprolol 200 mg/day<br>Diovan 320 mg/day<br>Eplerenone 50 mg/day<br>Torsemide 20 mg/day<br>Glimepiride 2 mg 2x/day<br>Trillipix 20 mg/day<br>Bayer Asprin 81 mg/day<br>Niaspan 1000 mg/day | Off Metoprolol<br>Off Diovan<br>Off Eplerenone<br>Off Torsemide<br>Glimepiride cut in ½ 1x/day<br>Trillipix 10 mg/day<br>Off Bayer Asprin<br>Niaspan reduced to ½ |
| #8 | 7.4 | 6.7 | 164 | NA | 115 | 163 | 122/68 | 116/70 | Metformin 1000 mg 2x/day<br>Glimepiride 4 mg 2x/day<br>Invokana 100 mg/day<br>Levemir 24 units<br>Metoprolol 100 mg 2x/day<br>Losartan 100 mg 2x/day<br>Ranitidine 150 mg 2x/day<br>Simvastatin 40 mg/day<br>Asprin 81 mg | Metformin 1000 mg am/500 mg pm<br>Off Glimepiride<br>Off Invokana<br>Off Levemir<br>Metoprolol 100 mg/day<br>Off Losartan<br>Ranitidine<br>Simvastatin 40 mg/day<br>Asprin 81 mg/day |
| #9 | | 5.9 | 173 | 155 | NA | 104 | 172/60 | 114/60 | Januvia 100 mg/day<br>Vytorin 10/40 mg<br>Norvasc 10 mg/day<br>Tekturna 150 mg | Off Januvia<br>Vytorin 10/40 mg<br>Off Norvasc<br>Off Tekturna |

TABLE 1-continued

| Patient | A1C Pre | A1C Post | Weight Pre | Weight Post | a1 Cholesterol Pre | a1 Cholesterol Post | Blood Pressure Pre | Blood Pressure Post | Meds/Dosage Pre | Meds/Dosage Post |
|---|---|---|---|---|---|---|---|---|---|---|
| #10 | 6.2 | 6 | 122.8 | 112 | 114 | 180 | 126/86 | 112/69 | Losortan 100 mg/day<br>Metformin 500 mg/day<br>Simvastatin 40 mg/day<br>Bayer Asprin 81 mg/day | Losortan 100 mg/day<br>Off Metformin<br>Off Simvastatin<br>Off Bayer Asprin |
| #11 | 7.1 | 6.1 | 177 | 169 | 154 | 188 | 146/86 | 123/64 | Lipitor 40 mg/day<br>Glipizide 10 mg/day<br>Lisinopril 40 mg | Off Lipitor<br>Glipizide 5 mg/day<br>Off Lisinopril |
| #12 | 6.3 | 5.9 | 250 | 215 | 138 | 98 | 127/70 | 131/70 | Metoprolol 50 mg 2x/day<br>Glipizide 10 mg 2x/day<br>Valsartan 80 mg/day<br>Simvastatin 20 mg 2x. day | Metoprolol 25 mg 2x/day<br>Off Glipizide<br>Valsartan 80 mg/day (for kidneys)<br>Simvastatin 10 mg/day |
| #13 | 6.3 | 5.6 | 185 | 185 | 193 | 176 | NA | NA | Glucophage 100 mg 2x/day<br>Januvia 100 mg/day<br>Lipitor 40 mg/day | Off Glucophage<br>Off Januvia<br>Off Lipitor |
| #14 | 6.8 | 6.3 | 217 | 189 | 137 | 172 | 107/75 | 115/73 | Novolog 24 units 3x/day<br>Lantus 52 units/day<br>Lisinopril 200 mg/day | Novolog 12 units/day<br>Lantus 8 units/day<br>Lisinopril 10 mg/day |
| #15 | 6.1 | 5.9 | 144 | 132 | 158 | 222 | NA | NA | Levothroxine 88 mcg/day<br>Metformin 100 mg 2x/day<br>Lisinopril/day<br>Lovastatin 40 mg/day<br>Lovaza 1 GM/day | Off Levothroxine<br>Off Metformin<br>Off Lisinopril<br>Off Lovastatin<br>Off Lovaza |
| #16 | 12.5 | 5.5 | 172 | 142 | 167 | 197 | 132/94 | 118/70 | Metformin 1000 mg/day<br>Metoprolol 25 mg<br>Allopurinol 100 mg<br>Lisinopril | Off Metformin<br>Off Metoprolol<br>Off Allopurinol<br>Off Lisinopril |
| #17 | 7.2 | 7 | 119 | 111 | 180 | 154 | NA | NA | Levimer 10 units<br>Humalog 24 unit 3x/day<br>Metformin 1000 mg/day<br>Lovastatin 20 mg/day | Off Levimer<br>Off Humalog<br>Metformin 1000 mg 2x/day<br>Off Lovastatin |
| #18 | 7.4 | 5.4 | 282 | 249 | 157 | 131 | 120/87 | 130/70 | Enalapril 20 mg/day<br>Glimepiride 20 mg/day<br>Losartan 100 mg/day | Enalapril 10 mg/day<br>Off Glimepiride<br>Losartan 50 mg/day |
| #19 | 7.6 | 6.7 | 168 | 152 | 171 | 170 | 120/80 | 147/68 | Januvia 100 mg/day<br>Enalapril 10 mg/day<br>Metformin 1000 mg 2x/day<br>Metoprolol 150 mg 2x/day<br>Primidone 150 mg 2x/day<br>Glimepiride 150 mg 2x/day<br>Niacin 500 mg 2x/day | Off Januvia<br>Off Enalapril<br>Metformin 500 mg 2x/day<br>Off Metoprolol<br>Off Primidone<br>Glimepiride 50 mg 2x/day<br>Off Niacin |
| #20 | 6.6 | 5.7 | 174 | 160 | 198 | 219 | 126/73 | 125/74 | Metformin 1000 mg 2x/day<br>Lisinopril 5 mg/day | Metformin 500 mg/day<br>Lisinopril 2.5 mg/day |

What is claimed is:

1. A method of treating Type 2 Diabetes in a subject, comprising the following steps:

following a meal plan based on specific allowed foods and specific avoided foods;

exercising at least 30 minutes a day for 5 days a week by walking, running or biking either outdoors or using a treadmill, an elliptical machine or a stationary bike, and taking a Supplement 1 and a Supplement 2 each day for the first 30 days of treatment, wherein Supplement 1 comprises 10 mcg of Zinc, 25 mcg of Copper, 10 mcg of Manganese, 695 mg of a blended substance consisting of Licorice Root, *Psyllium*, Oat Bran, Celery, Sweet Potato, Apple Pectin, Grapefruit Pectin, and 10 mg of Magnesium and wherein Supplement 2 comprises 30 mcg of Zinc, 45 mcg of Selenium, 75 mcg of Copper, 30 mcg of Manganese, 100 mcg of Chromium, 525 Lipase Activity Units, 150 mg of Garlic, 60 mg of Tumeric Root, 76 mg of a blended substance consisting of Tumeric Root, Garcinia Cambogia, Cinnamon Verum, Raspberry Ketones, *Rhodiola Crenulata* and Glucomannanase, and taking a Supplement 3 and a Supplement 4 each day for an interval of between 2 to 6 months after said first 30 days of treatment wherein the length of the interval depends on the severity of the subject's Type 2 Diabetes as determined by a professional providing said treatment, wherein Supplement 3 comprises 40 mg of Zinc, 50 mcg of Copper, 20 mcg of Manganese, 150 mg of Milk Thistle Extract, 200 mg of Bayberry Root, 200 mg of Dandelion Root and 400 Lipase Activity Units, and wherein supplement 4 comprises 1250 IU of Vitamin A, 15 mg of Vitamin C, 4100 IU of Vitamin D, 9.75 IU of Vitamin E, 20 mcg of Vitamin K, 120 mcg of Vitamin K2, 380 mcg of Vitamin B1, 500 mcg of Vitamin B2, 5 mg of Vitamin B3, 500 mcg of Vitamin B6, 100 mcg of Vitamin B9, 10 mcg of Vitamin B12, 10 mcg of Vitamin B7, 2.5 mg of Vitamin B5, 125 mg of Calcium, 4.5 mg of Iron, 50 mg of Magnesium, 4.04 mg of Zinc, 50 mcg of Selenium, 650 mcg of Copper, 500 mcg of Manganese, 100 mcg of Chromium, 20 mcg of Molybdenum, 9 mg of Potassium, 500 mg of a Stabilized Fatty Acid Blend consisting of Borage Oil, Flax Seed Oil, and Algae Oil, 415 mg of a whole food media blend consisting of an organic vegetable blend, an organic fruit blend, vitamins and probiotics, 100 mg of Garlic, 100 mg of Jerusalem Artichoke, 50.6 mg of a blend consisting of Cinnamon Verum, Raspberry Ketones, *Rhodiola* Crenulated and Glucomannanase, 40 mg of Turmeric, 30 mg of CoQ10 Ubiquinol, 5 mg of Black Strap Molasses, 40 mcg of Kelp, 170 Lipase Activity Units and 1.25 Billion CFU of Stabilized Heat Resistant Probiotics consisting of *Lactobacillus, Acidophilus*, L-*Plantarum, Bulgaricus, Streptococcus, Thermophilus* and *Enterococcus Faecium*.

2. The method of claim 1 wherein said Supplement 1 includes 10 mg of a delivery system consisting of Amylase, Protease I, Protease II, Lipase, Invertase, Cellulose, Lactase, Maltase, Hemiserb Zinc AAC, Copper AAC, Manganese AAC and Molasses.

3. The method of claim 1 wherein said Supplement 2 includes 30 mg of said delivery systems.

4. The method of claim 1 wherein Supplement 3 includes 20 mg of said delivery system.

5. The method of claim 1 wherein Supplement 4 includes 50 mg of said delivery system.

6. The method of claim 1 wherein the specific allowed foods are:
   cream of buckwheat;
   vegetables, wherein potatoes are excluded except for sweet potatoes and yams;
   beans and legumes, wherein soybeans are excluded;
   meats with no additives, wherein pork intake is limited;
   eggs;
   nuts and seeds, including nut butters;
   Quinoa;
   Amaranth;
   Sweeteners, including raw honey in limited amounts, molasses, *stevia*;
   Herbal and caffeine free teas;
   unsweetened almond milk;
   unsweetened coconut milk;
   lemon juice;
   lime juice;
   purified water; and
   fresh or frozen fruit with no added sugars or sweeteners, wherein pineapple, watermelon, and bananas are limited.

7. The method of claim 1 wherein the specific avoided foods are:
   all dairy;
   all wheat/rye/oat/barley;
   all soy products;
   all corn;
   all red and white potatoes;
   all alcohol;
   all juices except for lemon juice and lime juice;
   all caffeine;
   all carbonated beverages and sodas; and
   all sugar and artificial sweeteners.

* * * * *